United States Patent [19]

Hosokawa et al.

[11] Patent Number: 5,380,884
[45] Date of Patent: Jan. 10, 1995

[54] METHOD FOR PRODUCING GLYCIDYL METHACRYLATE

[75] Inventors: Hideo Hosokawa; Misao Shikatsu; Takahiro Fujimoto, all of Kashiwara, Japan

[73] Assignee: Osaka Organic Chemical Ind. Co., Ltd., Osaka, Japan

[21] Appl. No.: 226,054

[22] Filed: Apr. 11, 1994

[30] Foreign Application Priority Data

Jun. 17, 1993 [JP] Japan ................ 5-172735

[51] Int. Cl.$^6$ ................ C07D 301/28; C07D 301/32; C07D 303/12; C07D 303/38
[52] U.S. Cl. ................................ 549/515; 562/598
[58] Field of Search ........................ 549/515

[56] References Cited

U.S. PATENT DOCUMENTS

| | | | |
|---|---|---|---|
| 2,537,981 | 1/1951 | Edwards | 549/515 |
| 3,075,999 | 1/1963 | June et al. | 549/515 |
| 3,661,938 | 5/1972 | Heilman | 549/515 |
| 3,975,831 | 5/1976 | Heilman | 549/515 |
| 4,755,262 | 7/1988 | Matsunaga et al. | 549/515 |

FOREIGN PATENT DOCUMENTS

| | | |
|---|---|---|
| 0190609 | 8/1986 | European Pat. Off. |
| 52-25714 | 2/1977 | Japan . |
| 54-3007 | 1/1979 | Japan . |
| 55-94379 | 7/1980 | Japan . |
| 55-102575 | 8/1980 | Japan . |
| 56-118075 | 9/1981 | Japan . |
| 61-260893 | 11/1986 | Japan . |
| 63-255273 | 10/1988 | Japan . |
| 4-187682 | 7/1992 | Japan . |

*Primary Examiner*—Joseph E. Evans
*Attorney, Agent, or Firm*—Birch, Stewart, Kolasch & Birch

[57] ABSTRACT

Glycidyl methacrylate is produced by the reaction of an alkali metal salt of methacrylic acid with epichlorohydrin in the presence of a quaternary ammonium salt and a polymerization inhibitor in a reaction system where the water content is adjusted to 500 to 2000 ppm. Glycidyl methacrylate is purified by the method of the present invention, wherein the reaction mixture obtained by the above method is washed with a dilute aqueous solution of sodium hydroxide and heated under a reduced pressure to remove unchanged epichlorohydrin by distillation, after which steam is blown into the reaction system under the conditions of reduced pressure and heating to distill away the remaining epichlorohydrin together with glycidyl methacrylate as the first distillate fraction, followed by ceasing the steam blow and carrying out distillation under the conditions of reduced pressure and heating to obtain glycidyl methacrylate as the main distillate fraction.

14 Claims, No Drawings

METHOD FOR PRODUCING GLYCIDYL METHACRYLATE

BACKGROUND OF THE INVENTION

1. Field of the Invention

The present invention relates to a method for producing a low chlorine-containing and highly pure glycidyl methacrylate which substantially contains no epichlorohydrin.

2. Discussion of the Related Arts

Glycidyl methacrylate is usually produced by allowing methacrylic acid to react with epichlorohydrin to yield the chlorohydrin ester of methacrylic acid and subjecting the ester to dehydrochlorination. Alternatively, it is produced by the reaction of an alkali metal salt of methacrylic acid with epichlorohydrin in the presence of a quaternary ammonium salt as a catalyst.

The glycidyl methacrylate produced by these methods, however, contains residual chlorine compounds such as epichlorohydrin at 0.1 to 1.0% by weight, resulting in a decreased purity of glycidyl methacrylate and an increased content of free chlorine.

In order to decrease the content of free chlorine from epichlorohydrin and other chlorine compounds, several methods have been disclosed, which include the method in which azeotropic distillation is performed in two stages (French Patent No. 2656305) and the method in which distillation is performed after stripping with an oxygen-containing gas in the presence of a quaternary ammonium salt (Japanese Patent Laid-Open No. 4-187682). These methods, however, does not sufficiently accomplish their object because not less than 100 ppm of epichlorohydrin, etc. remains in the final product. The increase in the number of process steps due to these additional treatment is also a problem. On the other hand, it is known that the content of chlorine can be reduced by performing a treatment with a hetero poly acid after completion of the reaction and then performing distillation (Japanese Patent Laid-Open No. 63-255273). This method, however, uses an expensive hetero poly acid, and therefore a more economical method is desired.

Also, there are some theoretically chlorine-free methods based on an ester exchange reaction of methacrylic acid ester and glycidol (Japanese Patent Laid-Open Nos. 52-25714, 54-3007, 56-118075, 55-102575 and 55-94379 and many other publications). These methods, however, are not suitable for industrial production of glycidyl methacrylate because glycidol, the starting material, is so unstable in storage that its content decreases over time even at room temperature.

Other disclosed methods for production of glycidyl methacrylate include the method in which an allyl methacrylate is epoxidated with hydrogen peroxide [European Patent No. 190609, Chim. Ind. 72, 610–616 (1990)] and the method in which epoxidation is performed using a microorganism (Japanese Patent Laid-Open No. 61-260893). These methods, however, are not suitable for industrial production because the starting material does not suit for industrial use and because these methods are not economically favorable.

In conventional methods for production of glycidyl methacrylate, the reaction of an alkali metal salt of methacrylic acid with a 3–10 times higher molar amount of epichlorohydrin are carried out in the presence of 0.3 to 2.0 mol % of a quaternary ammonium salt as a catalyst and about 0.01 to 0.2% by weight of a polymerization inhibitor at a reaction temperature of 80° to 120° C. for 1 to 5 hours, and the by-produced salts are removed by filtration, washing with water and other means to yield crude glycidyl methacrylate, which is finally purified by distillation under reduced pressure.

The purified glycidyl methacrylate thus obtained contains 0.1 to 1.0% by weight of residual epichlorohydrin and at most 98.5% by weight of glycidyl methacrylate, showing a decreased purity of glycidyl methacrylate and an increased content of free chlorine.

In particular, acceleration of corrosion of metal substrate of electronic equipment by the increased free chlorine is a problem, because the main applications of glycidyl methacrylate include electronic materials such as paints and resists. Moreover, epichlorohydrin has toxic effects such as intense skin irritation, requiring special caution in handling glycidyl methacrylate which contains residual epichlorohydrin. In addition to these problems in safety, hygiene and environmental protection, there are also legal regulations.

SUMMARY OF THE INVENTION

The object of the present invention is to solve the technical problems in the prior arts and provide a simple method for producing glycidyl methacrylate of high purity and low chlorine content, which contains a decreased amount of chlorine compounds such as harmful epichlorohydrin.

The present inventors investigated a method for removing residual epichlorohydrin which is contained at 0.1 to 1.0% by weight in glycidyl methacrylate produced from an alkali metal salt of methacrylic acid and epichlorohydrin, and obtained an unexpected finding that the residual epichlorohydrin can easily be removed by controlling the water content in the reaction system for the synthesis of glycidyl methacrylate and by distilling the resulting glycidyl methacrylate with steam. Based upon this findings, the inventors made further studies and have completed the present invention.

Specifically, the gist of the present invention relates to:

(1) A method for producing glycidyl methacrylate, comprising the step of reacting an alkali metal salt of methacrylic acid with epichlorohydrin in the presence of a quaternary ammonium salt and a polymerization inhibitor, wherein the water content in the reaction system is adjusted to 500 to 2000 ppm; and (2) A method for producing purified glycidyl methacrylate, comprising the steps of washing the reaction mixture obtained by the above method (1) with a dilute aqueous solution of sodium hydroxide; heating under a reduced pressure to remove unchanged epichlorohydrin by distillation; blowing steam into the reaction system under the conditions of reduced pressure and heating to distill away the remaining epichlorohydrin together with glycidyl methacrylate as the first distillate fraction; and ceasing the steam blow and carrying out distillation under the conditions of reduced pressure and heating to obtain glycidyl methacrylate as the main distillate fraction.

By the use of the method for producing glycidyl methacrylate of the present invention, glycidyl methacrylate of high quality and with low content of chlorine compounds such as epichlorohydrin can be produced by easy and simple procedures.

DETAILED DESCRIPTION OF THE INVENTION

The present invention is hereinafter described in detail.

The alkali metal salt of methacrylic acid used for the present invention is prepared by; adding methacrylic acid to an aqueous solution of sodium hydroxide, potassium hydroxide or lithium hydroxide under cooling condition; neutralizing the solution; and then making the resulting substance a dry powder having a water content of 0.02 to 0.5%, preferably 0.05 to 0.2%, by hot-blow drying or another means.

The amount of epichlorohydrin used for the present invention is normally 2 to 15 mol, preferably 3 to 10 mol, per mol of the alkali metal salt of methacrylic acid. This is because amounts of less than 2 mol result in decreased yield, and amounts exceeding 15 mol causes an increased load, rather than an increased yield, upon purification of the reaction product.

The quaternary ammonium salts used as a catalyst for the present invention are exemplified by tetramethylammonium chloride, tetraethylammonium chloride, trimethylbenzylammonium chloride and triethylbenzylammonium chloride with a preference given to tetramethylammonium chloride. The amount of the catalyst used is normally 0.1 to 5.0 mol %, preferably 0.3 to 2.0 mol % relative to the alkali metal salt of methacrylic acid.

The polymerization inhibitors used for the present invention are exemplified by phenothiazine, hydroquinone, hydroquinone monomethyl ether and N,N'-diphenylparaphenylenediamine with a preference given to phenothiazine. The amount of polymerization inhibitor used is normally 0.005 to 1.0% by weight, preferably 0.01 to 0.2% by weight.

In the method for production of glycidyl methacrylate of the present invention, adjustment of the water content in the reaction system is the most important. When the desired amount of water is present in the reaction systems the reactivity of epichlorohydrin with the alkali metal salt of methacrylic acid increases and the selectivity improves, which in turn suppresses the by-production of impurities which hamper purification of glycidyl 10 methacrylate and removal of epichlorohydrin by distillation. The water content in the reaction mixture, which comprises an alkali metal salt of methacrylic acid, epichlorohydrin, a quaternary ammonium salt and a polymerization inhibitor, has been conventionally under 500 ppm at the time of mixing, as determined by Karl Fischer's method. In the present invention, the water content is adjusted to 500 to 2000 ppm, preferably 600 to 1600 ppm, more preferably 1100 to 1300 ppm. If the water content is under 500 ppm, the concentration of impurities such as glycidol, dichlorohydrin and diglycidyl ether, whose boiling points are near the boiling point of glycidyl methacrylate, increases, so that the removal of these impurities by distillation become difficult and high quality glycidyl methacrylate cannot be obtained. If the water content exceeds 2000 ppm, the increased reactivity leads to increased production of glycerol dimethacrylate and trimethacrylate because glycidyl methacrylate produced is further attacked by methacrylate. Although these can be separated and purified by distillation, reduction in yield is inevitable. Also, the production of the high-boiling-point components hampers separation by washing, causing decreased operation efficiency as well as decreased yield.

In the present invention, the water content in the reaction system is adjusted to the desired level by, for example, adding water to the reaction system. Other reaction conditions are not subject to limitation. Conditions used in ordinary methods for producing glycidyl methacrylate can be employed. Specifically, reaction temperature is 80° to 120° C., and reaction time is normally 1 to 5 hours, although it varies depending on reaction temperature.

This reaction is an exothermic reaction; after heat generation has ceased, ripening is carried out for a given period of time, after which an amount of glycidyl methacrylate is determined by GC analysis of the reaction mixture to decide the reaction end point. GC analysis can be performed by raising the column temperature from 70° C. to 250° C. at a rate of 5° C./min (TCD detection, silicon GE60, 10%, 1.5 m glass column).

The glycidyl methacrylate obtained by the production method of the present invention is purified by the purification method of the present invention which purposes complete removal of epichlorohydrin. First, the reaction mixture is mixed and stirred with an almost equal amount of a dilute aqueous solution of sodium hydroxide (2 to 5%) and kept standing, and the water layer is removed, followed by 2 to 3 times of washing with distilled water to obtain a crude glycidyl methacrylate layer (washing process). To remove the unchanged epichlorohydrin from the crude glycidyl methacrylate, the crude glycidyl methacrylate layer is distilled under a reduced pressure of 70 to 50 mm Hg at a bottom temperature of about 55° C. (concentration process).

Next, to remove the residual epichlorohydrin and chlorine-containing by-products such as 1,3-dichloro-2-propanol, 2,3-dichloro-1-propanol and 2-hydroxy-3-chloropropyl methacrylate, distillation under reduced pressure is performed while steam is blown in, whereby these chlorine-containing compounds are distilled away in the initial distillate fraction along with glycidyl methacrylate.

Although the amount of steam blown in varies depending on the apparatus used, it is normally 1 to 5% by weight, preferably 1 to 3% by weight relative to the total amount of distillate fractions taken out. Amounts of steam under 1% are undesirable because the chlorine content in glycidyl methacrylate increases due to insufficient removal of chlorine-containing compounds. If the amount of steam exceeds 5%, the yield of glycidyl methacrylate decreases. Some polymerization inhibitors are distilled away along with steam, and causes polymerization during the period from initial distillation to main distillation, which lowers the yield. Distillation is normally carried out under a reduced pressure of 30 to 13 mm Hg at a tower temperature of 36° to 68° C. and a bottom temperature of 60° to 85° C.

After the initial distillate fraction is separated, the steam blow is stopped. Then the main distillation is performed under the following conditions to obtain purified glycidyl methacrylate in the main distillate fraction. Specifically, main distillation is performed under a reduced pressure of 13 to 3 mm Hg at a tower temperature of 65° to 66° C. and a bottom temperature of 85° to 100° C. GC analysis of the main distillate fraction thus obtained and its chemical analysis for chlorine reveal that the glycidyl methacrylate content is not less than 99.0% and the epichlorohydrin content is not more than 40 ppm.

The conditions of GC analysis are FID detection; $H_2$, 0.5 kg/cm$^2$; air, 0.6 kg/cm$^2$; 20M capillary column, 25 m; column temperature 100° C.; heating to 200° C. at 8° C./min; injection temperature 250° C.; and carrier gas $N_2$, 50 ml/min.

Chlorine analysis is performed as follows: In a condenser equipped with a drying tube, the reaction of ethylenediamine with glycidyl methacrylate is allowed to occur by refluxing for 1 hour, and the amount of ethylenediamine consumed by the chlorine compounds contained in the glycidyl methacrylate is determined by back titration with 0.1N alcoholic KOH ($A_{20}$ Violet indicator is used).

EXAMPLES

The present invention is hereinafter described in more details by means of the following working examples, but the present invention is not limited by them.

Example 1

Preparation of sodium methacrylate:

After 5 kg (37.5 mol) of a 30% aqueous solution of sodium hydroxide was cooled below 60° C., 3.23 kg (37.5 mol) of methacrylic acid was added drop by drop while stirring. The aqueous solution of sodium methacrylate obtained by the neutralization reaction was spray-dried with 300° C. hot air to yield 4.04 kg of a dry powder of sodium methacrylate. The water content of this powder was 0.08%.

Synthesis of glycidyl methacrylate:

To a reaction vessel equipped with a stirrer, a thermometer and a reflux condenser, 3.5 kg (32.38 mol) of sodium methacrylate and 16.48 kg (178.10 mol) of epichlorohydrin were placed. After the water content in the reaction system was determined by Karl Fischer's method, water was added to adjust the water content in the system to 1100 ppm.

Then, 17.8 g (0.16 mol, 0.5 mol % relative to sodium methacrylate) of tetramethylammonium chloride as a catalyst and 5.25 g (0.15% by weight relative to sodium methacrylate) of phenothiazine as a polymerization inhibitor were added, and a reaction was allowed to occur at 90° C. for 5 hours while stirring the mixture.

After the completion of the reaction, each product in the reaction mixture was determined by GC analysis. The result was that substances whose boiling points are lower than the boiling point of glycidyl methacrylate, such as glycidol, were present at 0.38%, diglycidyl ether, dichlorohydrin, etc. at 0.30%, 1,3- or 1,2-dimethacrylate of glycerol at 1.1%, glycerol trimethacrylate at 3.3%, and glycidyl methacrylate at 94.9%.

Next, 6 kg of a 3% aqueous solution of sodium hydroxide was added to the reaction mixture, followed by mixing and stirring, after which the mixture was kept standing to separate an ester layer and a water layer. After the water layer was removed, the ester layer was washed with distilled water to yield crude glycidyl methacrylate.

Purification of crude glycidyl methacrylate:

The crude glycidyl methacrylate thus obtained was concentrated at a still temperature of about 60° C. under a pressure of 50 to 70 mm Hg using a 10-stage lift tray to remove and recover the unchanged epichlorohydrin (13.09 kg).

Next, while steam was adjusted to blow in an amount of 2% by weight relative to the amount of distillate fraction, distillation was performed under a reduced pressure of 30 to 13 mm Hg at a still temperature of about 85° C. and an tower top temperature of 36° to 68° C. to recover the remaining epichlorohydrin along with glycidyl methacrylate in 1.372 kg of the first distillate fraction.

After steam blow was stopped, distillation was performed under a reduced pressure of 3 mm Hg at a still temperature of about 85° C. and an tower top temperature of 65° to 66° C. to yield 4.235 kg of purified glycidyl methacrylate. The product yield was 92% by weight.

GC analysis showed that the purified glycidyl methacrylate thus-obtained was of high quality, comprising 99.2% of glycidyl methacrylate, 33 ppm of epichlorohydrin and 0.10% of chlorine.

Example 2

Employing the same conditions as in Example 1, the synthesis of glycidyl methacrylate was carried out by varying the content of water in the reaction system from 300 ppm to 2500 ppm, and the products in the reaction mixture were analyzed by GC. The results of the analysis are shown in Table 1.

TABLE 1

| Water content of the reaction system (ppm) | Amounts of reaction products (%) | | | | |
|---|---|---|---|---|---|
| | glycidol | diglycidyl ether, dichlorohydrin | glycerol dimethacrylate | glycerol trimethacrylate | glycidyl methacrylate |
| 300 | 0.84 | 0.70 | 0.3 | 2.7 | 95.46 |
| 500 | 0.68 | 0.56 | 0.5 | 2.9 | 95.36 |
| 600 | 0.60 | 0.50 | 0.6 | 3.0 | 95.30 |
| 800 | 0.48 | 0.40 | 0.8 | 3.1 | 95.22 |
| 1000 | 0.40 | 0.32 | 1.0 | 3.2 | 95.08 |
| 1100 | 0.38 | 0.30 | 1.1 | 3.3 | 94.92 |
| 1300 | 0.34 | 0.27 | 1.3 | 3.3 | 94.79 |
| 1600 | 0.29 | 0.24 | 1.6 | 3.4 | 94.47 |
| 2000 | 0.24 | 0.20 | 1.8 | 3.4 | 94.36 |
| 2500 | 0.20 | 0.16 | 2.3 | 3.4 | 93.94 |

The results indicate that the amount of glycidol and other by-products, which hamper the purification of glycidyl methacrylate, increases when the content of water in the reaction system is less than 500 ppm and that the amounts of glycerol dimethacrylate produced increase when the water content is higher than 2000 ppm.

Example 3

Crude glycidyl methacrylate was produced in the same manner as in Example 2. Samples of crude glycidyl methacrylate produced in the reaction systems with water contents of 300 ppm, 1100 ppm and 1600 ppm were respectively subjected to an analysis to know how the amount of steam blow in the purification process affects the reaction products. The results are shown in Table 2.

TABLE 2

| Water content of the reaction system (ppm) | Amount of steam (% by weight) | Glycidyl methacrylate (%) | Epichlorohydrin (ppm) | Chlorine (%) | Yield (%) |
|---|---|---|---|---|---|
| 300 | 0 | 96.1 | 4600 | 0.52 | 88 |
| | 2 | 97.6 | 47 | 0.17 | 87 |
| 1100 | 0 | 98.0 | 3800 | 0.40 | 92 |
| | 1 | 99.0 | 37 | 0.10 | 92 |

TABLE 2-continued

| Water content of the reaction system (ppm) | Amount of steam (% by weight) | Glycidyl methacrylate (%) | Epichlorohydrin (ppm) | Chlorine (%) | Yield (%) |
|---|---|---|---|---|---|
| | 2 | 99.2 | 33 | 0.10 | 92 |
| | 5 | 99.0 | 27 | 0.10 | 90 |
| 1600 | 2 | 98.9 | 33 | 0.12 | 87 |

As clearly shown in Table 2, when the amount of steam blow was 0%, 3800 to 4600 ppm of residual epichlorohydrin was present. To the contrary, when the amount of steam was increased to 2 to 5%, residual epichlorohydrin was decreased below 40 ppm (except when the water content of the reaction system was 300 ppm). It is also shown that the purification efficiency of the crude glycidyl methacrylate obtained in the reaction system with water content of 300 ppm is lower than that obtained in the reaction system with water content of 1100 ppm.

The present invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for producing glycidyl methacrylate, comprising the step of reacting an alkali metal salt of methacrylic acid with epichlorohydrin in the presence of a quaternary ammonium salt and a polymerization inhibitor, wherein the water content in the reaction system is adjusted to 500 to 2000 ppm.

2. The method according to claim 1, wherein said water content in the reaction system is adjusted to 600 to 1600 ppm.

3. The method according to claim 1, wherein said alkali metal salt of methacrylic acid is obtained by adding methacrylic acid to an aqueous solution of sodium hydroxide, potassium hydroxide or lithium hydroxide under cooling condition, neutralizing the solution, and then making the resulting substance a dry powder having a water content of 0.02 to 0.5%.

4. The method according to claim 3, wherein said dry powder has a water content of 0.05 to 0.2%.

5. The method according to claim 1, wherein the amount of epichlorohydrin is 2 to 15 mol per mol of the alkali metal salt of methacrylic acid.

6. The method according to claim 5, wherein said amount of epichlorohydrin is 3 to 10 mol per mol of the alkali metal salt of methacrylic acid.

7. The method according to claim 1, wherein said quaternary ammonium salt is one member selected from the group consisting of tetramethylammonium chloride, tetraethylammonium chloride, trimethylbenzylammonium chloride and triethylbenzylammonium chloride.

8. The method according to claim 1, wherein the amount of said quaternary ammonium salt is 0.1 to 5.0 mol %, relative to the alkali metal salt of methacrylic acid.

9. The method according to claim 8, wherein said amount of the quaternary ammonium salt is 0.3 to 2.0 mol %, relative to the alkali metal salt of methacrylic acid.

10. The method according to claim 1, wherein said polymerization inhibitor is one member selected from the group consisting of phenothiazine, hydroquinone, hydroquinone monomethyl ether and N,N'-diphenyl-paraphenylenediamine.

11. The method according to claim 1, wherein the amount of said polymerization inhibitor is 0.005 to 1.0% by weight.

12. The method according to claim 11, wherein said amount of the polymerization inhibitor is 0.01 to 0.2% by weight.

13. The method according to claim 1, wherein the water content in the reaction system is adjusted by adding water to the reaction system.

14. A method for producing purified glycidyl methacrylate, comprising the steps of:
   washing the reaction mixture obtained by claims 1, 2, 3, 4, 5, 6, 7, 8, 9, 10, 11, 12 or 13 with a dilute aqueous solution of sodium hydroxide;
   heating under a reduced pressure to remove unchanged epichlorohydrin by distillation;
   blowing steam into the reaction system under the conditions of reduced pressure and heating to distill away the remaining epichlorohydrin together with glycidyl methacrylate as the first distillate fraction; and
   ceasing the steam blow and carrying out distillation under the conditions of reduced pressure and heating to obtain glycidyl methacrylate as the main distillate fraction.

* * * * *